(12) United States Patent
Gyakushi et al.

(10) Patent No.: US 8,985,399 B2
(45) Date of Patent: Mar. 24, 2015

(54) KNOCK-TYPE EJECTION CONTAINER

(75) Inventors: Hidetoshi Gyakushi, Tokyo (JP); Nobutoshi Yamaguchi, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 0 days.

(21) Appl. No.: 13/820,529

(22) PCT Filed: Sep. 5, 2011

(86) PCT No.: PCT/JP2011/070127
§ 371 (c)(1),
(2), (4) Date: Mar. 4, 2013

(87) PCT Pub. No.: WO2012/033037
PCT Pub. Date: Mar. 15, 2012

(65) Prior Publication Data
US 2013/0175300 A1 Jul. 11, 2013

(30) Foreign Application Priority Data

Sep. 7, 2010 (JP) .................. 2010-199737
Oct. 4, 2010 (JP) .................. 2010-224675

(51) Int. Cl.
*B67D 7/06* (2010.01)
*B65D 35/24* (2006.01)
*A61C 5/06* (2006.01)
*A61M 3/00* (2006.01)

(52) U.S. Cl.
CPC ............... *B65D 35/24* (2013.01); *A61C 5/062* (2013.01); *A61M 3/00* (2013.01)

USPC ................ 222/183; 222/386; 222/420

(58) Field of Classification Search
USPC ......... 222/131, 183, 156, 189, 420, 386, 282, 222/309; 433/89, 90; 604/187–199, 604/218–233, 68–72; 401/3, 126, 133
See application file for complete search history.

(56) References Cited

U.S. PATENT DOCUMENTS

| 987,169 | A | * | 3/1911 | Reimann ..................... 401/2 |
| 1,935,639 | A | * | 11/1933 | Keeshan ..................... 401/192 |
| 4,121,600 | A | * | 10/1978 | Riddick et al. ............... 132/310 |

(Continued)

FOREIGN PATENT DOCUMENTS

| JP | 09-150856 | 6/1997 |
| JP | 10-175683 | 6/1998 |

(Continued)

OTHER PUBLICATIONS

International Search Report filed on PCT/JP2011/070127.

*Primary Examiner* — J. Casimer Jacyna
*Assistant Examiner* — Randall Gruby
(74) *Attorney, Agent, or Firm* — Rankin, Hill & Clark LLP (57) ABSTRACT

[Problems] To provide an ejection container capable of falling a liquid in drops from the container body without relying on the sense of the fingertips and without affected by a change in the temperature.
[Means for Solution] A knock-type ejection container 1 in which an ejection port 8 is provided at one end of a container body 2, a knock button 4 is provided at the other end thereof, a container chamber 22 is provided in the container body 2 to contain a liquid, and the liquid contained in the container chamber 22 is ejected from the ejection port 8 being interlocked to the operation of the knock button 4.

8 Claims, 8 Drawing Sheets (56) References Cited

U.S. PATENT DOCUMENTS

| | | | | |
|---|---|---|---|---|
| 4,624,594 A * | 11/1986 | Sasaki et al. | | 401/176 |
| 4,726,386 A * | 2/1988 | Schultz | | 132/317 |
| 4,750,502 A * | 6/1988 | Ser et al. | | 132/74.5 |
| 4,773,785 A * | 9/1988 | Katz | | 401/101 |
| 4,813,870 A * | 3/1989 | Pitzen et al. | | 433/90 |
| 4,874,117 A * | 10/1989 | Kay et al. | | 222/487 |
| 4,892,427 A * | 1/1990 | Ford | | 401/182 |
| 4,958,748 A * | 9/1990 | Otake | | 222/131 |
| 4,997,299 A * | 3/1991 | Ohba | | 401/75 |
| 5,026,195 A * | 6/1991 | Kimura | | 401/283 |
| 5,035,525 A * | 7/1991 | Konose | | 401/278 |
| 5,046,648 A * | 9/1991 | Herbstzuber | | 222/638 |
| 5,098,291 A * | 3/1992 | Curtis et al. | | 433/89 |
| 5,137,388 A * | 8/1992 | Kimura | | 401/278 |
| 5,156,479 A * | 10/1992 | Iizuka | | 401/151 |
| 5,183,182 A * | 2/1993 | Comstock et al. | | 222/129 |
| 5,300,030 A * | 4/1994 | Crossman et al. | | 604/136 |
| 5,316,193 A * | 5/1994 | Heiberger | | 222/131 |
| 5,556,468 A * | 9/1996 | Legrain et al. | | 118/202 |
| 5,827,002 A * | 10/1998 | Nakajima | | 401/174 |
| 5,842,609 A * | 12/1998 | Higgins et al. | | 222/181.3 |
| 5,851,079 A * | 12/1998 | Horstman et al. | | 401/174 |
| 5,879,336 A * | 3/1999 | Brinon | | 604/191 |
| 6,041,952 A * | 3/2000 | Martin | | 215/12.1 |
| 6,053,893 A * | 4/2000 | Bucher | | 604/131 |
| 6,109,484 A * | 8/2000 | Sueoka et al. | | 222/390 |
| 6,391,003 B1 * | 5/2002 | Lesch, Jr. | | 604/110 |
| 6,474,891 B1 * | 11/2002 | Liu | | 401/174 |
| 6,524,102 B2 * | 2/2003 | Davis | | 433/32 |
| 6,530,709 B1 * | 3/2003 | Washington | | 401/272 |
| 6,689,101 B2 * | 2/2004 | Hjertman et al. | | 604/131 |
| 6,986,758 B2 * | 1/2006 | Schiffmann | | 604/131 |
| 7,448,814 B2 * | 11/2008 | Bouix et al. | | 401/2 |
| 7,500,966 B2 * | 3/2009 | Hommann | | 604/211 |
| 7,794,166 B2 * | 9/2010 | Zhang | | 401/179 |
| 7,883,286 B2 * | 2/2011 | Thiebaut | | 401/78 |
| 8,092,108 B2 * | 1/2012 | Bainbridge et al. | | 401/171 |
| 8,226,319 B2 * | 7/2012 | Francavilla et al. | | 401/278 |
| 8,276,597 B1 * | 10/2012 | Harden | | 132/200 |
| 8,328,449 B2 * | 12/2012 | Wightman et al. | | 401/174 |
| 8,506,194 B2 * | 8/2013 | Liu | | 401/175 |
| 8,602,774 B2 * | 12/2013 | Wasylucha | | 433/89 |
| 2002/0070247 A1 * | 6/2002 | Kageyama et al. | | 222/386 |
| 2003/0102334 A1 * | 6/2003 | Usami et al. | | 222/386 |
| 2005/0063766 A1 * | 3/2005 | Chen et al. | | 401/179 |
| 2006/0206057 A1 * | 9/2006 | DeRuntz et al. | | 604/224 |
| 2007/0020038 A1 * | 1/2007 | Tani | | 401/265 |
| 2007/0025804 A1 * | 2/2007 | Zhang et al. | | 401/174 |
| 2007/0086830 A1 * | 4/2007 | Kageyama | | 401/172 |
| 2008/0112752 A1 * | 5/2008 | Zhang | | 401/174 |
| 2009/0060624 A1 * | 3/2009 | Schenck et al. | | 401/171 |
| 2009/0097899 A1 * | 4/2009 | Carroll | | 401/109 |
| 2010/0036318 A1 * | 2/2010 | Raday et al. | | 604/134 |
| 2011/0116857 A1 * | 5/2011 | Carroll et al. | | 401/101 |
| 2011/0129288 A1 * | 6/2011 | Uehara | | 401/152 |
| 2011/0182649 A1 * | 7/2011 | Rolion et al. | | 401/55 |
| 2011/0250007 A1 * | 10/2011 | Kang | | 401/179 |
| 2012/0043350 A1 * | 2/2012 | Kojima et al. | | 222/183 |
| 2012/0148330 A1 * | 6/2012 | Yoon | | 401/32 |
| 2013/0032241 A1 * | 2/2013 | Yamaguchi et al. | | 141/2 |

FOREIGN PATENT DOCUMENTS

| | | |
|---|---|---|
| JP | 10-245080 | 9/1998 |
| JP | 2000-083967 | 3/2000 |
| JP | 2000-262544 | 9/2000 |
| JP | 2000-281112 | 10/2000 |
| JP | 2006-273336 | 10/2006 |

* cited by examiner

KNOCK-TYPE EJECTION CONTAINER

TECHNICAL FIELD

This invention relates to a knock-type ejection container which is capable of dropping a liquid in a suitable amount from the container body maintaining stability without relying on the gap of the fingertips, being not accompanied by a problem from the hygienic point of view, preventing the liquid from unnecessarily ejected at the time of ejection that is caused by an increase in the pressure in the container as a result of volatilization and expansion of liquid in the container body due to a rise in the temperature, and preventing the liquid from rising and creeping around the ejection portion from an ejection port in the ejection portion such as nozzle at the time when the fluid in the container body is ejected.

BACKGROUND ART

In the field of dental treatment, a resin material called resin composite is used for restoring a decayed tooth of a relatively light degree. To restore the decayed tooth by using the resin composite, the decayed portion of the tooth is removed by grinding, the portion that is missing by grounding is pre-treated with an etching material, a cured layer of a curable composition called bonding material is formed thereon so as to exhibit a high adhesive property to the resin composite, and the resin composite is adhered onto the layer of the bonding material. As the bonding material, there can be used a liquid curable composition of either the photo-curing type or the chemical-curing type.

The dental material is contained in a container body made of a plastic. At the time of use, the container is pushed by fingertips to produce pressure in the container body so that the material falls down in drops from an ejection port.

Namely, the following document 1 discloses a liquid container of the one-push squeeze type according to which the container is held between the thumb and the forefinger or the middle finger to pressurize the liquid-containing chamber in the container so that the liquid in the liquid-containing chamber flows out in drops in a required amount from an opening at an end of the nozzle. Upon removing the pressure from the liquid-containing chamber, the liquid in the opening at the end of the nozzle is sucked into the container back due to the resilience force of the container. The liquid container of the squeeze type is simple in the structure permitting the liquid contained in the container chamber to fall down in drops from the opening at the end of the nozzle by simply pushing the container body and has, therefore, been frequently used as a container for containing the dental bonding materials.

Some dental materials are highly volatile. When the container body is gripped by hand, therefore, the temperature of the human body is conducted to the interior of the container body through the outer circumferential wall thereof, and the adhesive volatilizes due to an increase in the temperature and is often ejected more than necessary through the ejection port. In particular, the adhesive is often preserved in a refrigerator. When the adhesive is taken out from the refrigerator, therefore, the temperature may rise to a considerable degree to hinder its use.

Therefore, the container disclosed in the patent document 1 is provided with a separate bag-like envelope that surrounds the bottom portion and the body portion of the container body. In the envelope, gaps formed among the ribs extending in the up-and-down direction play the role of a heat-insulating material preventing a rise in the temperature in the container body and enabling the liquid to be dripped in a desired amount responsive to the operation by fingertips.

The following patent document 2 discloses a knock-type container that can be used as a writing instrument storing such a liquid as ink, Japan ink or paint, as a makeup article storing such a liquid as eye liner, lip color or manicure, as a medicine container storing such a liquid as eye lotion, antiseptic solution or antibiotic, or as an application instrument storing such a liquid as seasoning, machine oil or washing solution.

The knock-type ejection container has a brush ear of a circular shape in cross section at an ejection portion at an end thereof, and has a knock button at the other end thereof. Responsive to each push of the knock button, a piston member pressurizes the liquid in the reservoir chamber, and the liquid is pushed out to the brush ear. With the brush ear being soaked with the liquid, the liquid contained therein is applied at the time of use onto an object.

Like the patent document 1, the following patent document 3 discloses a liquid container of the one-push squeeze type according to which the container is held between the thumb and the forefinger or the middle finger to pressurize the liquid-containing chamber in the container so that the liquid in the liquid-containing chamber flows out in drops in a required amount from an opening at an end of the nozzle. Upon removing the pressure from the liquid-containing chamber, the liquid in the opening at the end of the nozzle is sucked into the container back due to the resilience force of the container. The liquid container of the squeeze type is simple in the structure permitting the liquid contained in the container chamber to flow down in drops from the opening at the end of the nozzle by simply pushing the container body and has, therefore, been frequently used as a container for containing the dental bonding materials.

PRIOR ART DOCUMENTS

Patent Documents

Patent document 1: JP-A-10-175683
Patent document 2: JP-A-2000-281112
Patent document 3: JP-A-9-150856

OUTLINE OF THE INVENTION

Problems that the Invention is to Solve

According to the technology of the patent document 1 as described above, the container body is held between the thumb and the forefinger (or middle finger, too, is used), and the dental material is caused to flow down in drops from the container body. Therefore, the amount of flowing the dental material in drops is adjusted relying only upon the gap of the fingertips. As the liquid contained therein decreases, therefore, the air enters into the container body causing a change in the pressure of pushing, resulting in a change in the sense of the fingertips and often making the adjustment difficult.

According to the technology of the patent document 2, the liquid is used in a state in which the brush ear has been soaked with the liquid. When it is attempted to apply the dental material directly onto the diseased part by using the knock-type ejection container, therefore, it becomes necessary to renew or clean the brush ear from the hygienic point of view involving difficulty. Further, the knock-type ejection container produces no suction force based on the restoring force of the container when the pressure is removed from the liquid-containing chamber unlike the one-push squeeze type liquid container or only weakly produces the suction force even when a mechanism is provided to produce the suction force. When the container is used no longer, therefore, the liquid with which the brush ear is soaked mostly remains staying in the brush ear. Therefore, the liquid solidifies as the brush ear dries after the use. From this point of view, too, the brush ear must be frequently renewed. Otherwise, the liquid contained therein cannot be smoothly applied.

The knock-type container has an advantage in that it is capable of flowing down the solution in drops in a predetermined amount without relying upon the gap of the fingertips. However, the knock-type container is used being gripped by four fingers other than the thumb and by the palm of the hand permitting the human body temperature to be transmitted to the container to warm it and, therefore, causing a sharp rise in the temperature in the container. In this case, there will be no problem if the material is not volatile. If the material is volatile, however, there often occurs a phenomenon in that the liquid contained therein flows more than necessary to the brush ear against the will of the operator despite the knock button has not been operated.

With the squeeze-type liquid container as described above, the dental bonding material falls down in drops from the container. In flowing the dental bonding material down in drops, however, it often happens that the liquid ejected from the nozzle opening does not separate away from the nozzle opening and does not return into the nozzle despite the pressure is removed from the container (this phenomenon is also called liquid stay, see liquid stay b in FIG. 9B). A dentist at the time of use may incline the end of the nozzle. In such a case, the liquid that remains on the outside of the nozzle opening may rise and creep about the outer circumferential surface of the nozzle to adhere thereon. In a state where the liquid is adhering in a large amount, the liquid that is adhering and the liquid that drops next fall down in combination; i.e., the liquid is not often fed in a predetermined amount. Further, if the liquid adheres surrounding the nozzle, then the nozzle may be fouled. To prevent this, the patent document 3 discloses an art of suitably changing the shape of the nozzle end so that the remaining liquid will not concentrate at one place of the nozzle.

The present invention was accomplished in view of the above circumstances, and has an object of providing a knock-type ejection container which is capable of flowing a liquid down in drops from the container body without relying on the sense of the fingertips, preventing or suppressing the liquid from gushing despite of an increase in the temperature, and preventing the liquid from creeping around the ejection portion such as the nozzle without accompanied by a problem even from the standpoint of sanitation.

Means for Solving the Problems

In order to achieve the above object, the present invention provides a knock-type ejection container in which an ejection nozzle is provided at one end of a container body, a knock button is provided at the other end thereof, a container chamber is provided in the container body to contain a liquid dental material, and the dental material contained in the container chamber falls down in drops from the ejection nozzle being interlocked to the operation of pushing the knock button.

In the above knock-type ejection container, it is desired that at least the container chamber is surrounded by a double-wall structure comprising an inner circumferential wall and an outer circumferential wall, and a heat-insulating portion is provided between the inner circumferential wall and the outer circumferential wall.

In the above knock-type ejection container, the heat-insulating portion is the air filled in gap portions formed between the outer circumferential wall and the inner circumferential wall.

In the above knock-type ejection container, the outer circumferential wall is detachably fitted to the inner circumferential wall.

In the above knock-type ejection container, at least part of the inner circumferential wall is formed of a transparent material or a slit is perforated therein enabling the amount of the dental material contained therein to be recognized from the outer side.

In the above knock-type ejection container, the ejection nozzle includes a nozzle end portion on the front end side and a nozzle body on the rear end side, and a stepped surface is formed at a boundary portion between the nozzle end portion and the nozzle body over the whole circumference of the nozzle end portion, the stepped surface having a diameter expanding from the outer circumferential surface of the nozzle end portion toward the outer side in the radial direction.

In the above knock-type ejection container, if the amount of a drop discharged from the nozzle portion by the knock button push-in operation is denoted by V, the inner diameter of the ejection port of the nozzle end portion by D1, the outer diameter of the ejection port of the nozzle end portion by D2, the outer diameter of the stepped surface by D3, and the length from the ejection port of the nozzle end portion to the stepped surface by H, then the inner diameter D1 of the ejection port is set to be $aV^{1/3}$ (a is in a range from 0.5 to 0.7), the outer diameter D2 of the ejection port is set to be $bV^{1/3}$ (b is in a range from 0.8 to 1.1), the outer diameter D3 of the stepped surface is set to be $cV^{1/3}$ (c is in a range from 1.3 to 1.7), and the length H from the ejection port of the nozzle end portion to the stepped surface is set to be $dV^{1/3}$ (d is a range from 1.0 to 1.2), in a manner that D1, D2, D3 and H are all satisfied.

In the above knock-type ejection device, it is desired that a drop of liquid is fallen down from the ejection portion by the operation of pushing the knock button two or more times.

In the above knock-type ejection device, it is desired that the solution is a dental bonding material.

Effects of the Invention

In the knock-type ejection container of the present invention, an ejection nozzle is provided at one end of a container body, a knock button is provided at the other end thereof, a container chamber is provided in the container body to contain a liquid dental material, and the dental material contained in the container chamber falls down in drops from the ejection nozzle being interlocked to the operation of pushing the knock button making it possible to flow down the dental material in drops in a suitable amount maintaining stability without relying upon the sense of the fingertips. Besides, the dental material in the container is ejected dropwise from the ejection nozzle, which is efficient without requiring the renewal or cleaning of the ejection portion in a short period of time unlike that of the case of using the brush ear.

In the above knock-type ejection container, at least the container chamber is surrounded by a double-wall structure comprising an inner circumferential wall and an outer circumferential wall, and a heat-insulating portion is provided between the inner circumferential wall and the outer circumferential wall. Therefore, despite the container body is gripped by the palm of the hand and fingers, the body temperature is prevented from being conducted to the container chamber suppressing the volatilization particularly when a highly volatile dental material is used. Besides, the heat-insulating portion is the air that is present in the gap portions formed between the outer circumferential wall and the inner circumferential wall without requiring any particular heat-insulating material.

In the above knock-type ejection container, the outer circumferential wall is detachably fitted to the inner circumferential wall. Therefore, when a less volatile dental material is to be contained, the container is used with no outer circumferential wall fitted thereto and when a more volatile dental material is to be contained, the container is used with the outer circumferential wall fitted thereto improving general utility of the container.

In the above knock-type ejection container, the state of the dental material contained in the container body can be recognized through the outer circumferential wall and the inner circumferential wall facilitating the use of the container.

In the above knock-type ejection container, the ejection nozzle includes a nozzle end portion on the front end side of the nozzle and a nozzle body on the rear end side, and a stepped surface is formed at the boundary portion between the nozzle end portion and the nozzle body over the whole circumference of the nozzle end portion, the stepped surface having a diameter expanding from the outer circumferential surface of the nozzle end portion toward the outer side in the radial direction and suppressing the liquid from creeping around to the nozzle body when the liquid is ejected from the nozzle portion by pushing the knock button. This suppresses the liquid stay from growing.

In the above knock-type ejection device, a drop of liquid is fallen down from the ejection portion by the operation of pushing the knock button two or more times.

That is, a nucleus of a liquid drop is formed first and, thereafter, the liquid is added in an amount to let it drop, suppressing the formation of a liquid stay more reliably than when a drop of liquid is caused to fall by the operation of only one time of push.

BRIEF DESCRIPTION OF THE DRAWINGS

FIG. 9A is an enlarged view of the ejection portion in a state where a liquid stay is forming from the ejection portion having a stepped surface in the fifth embodiment of the present invention, and B is an enlarged view of the ejection portion in a state where a liquid stay is forming from the ejection portion without stepped surface according to a prior art.

MODES FOR CARRYING OUT THE INVENTION

The knock-type ejection container according to the embodiments of the invention will now be described with reference to the drawings.

Figure 1:
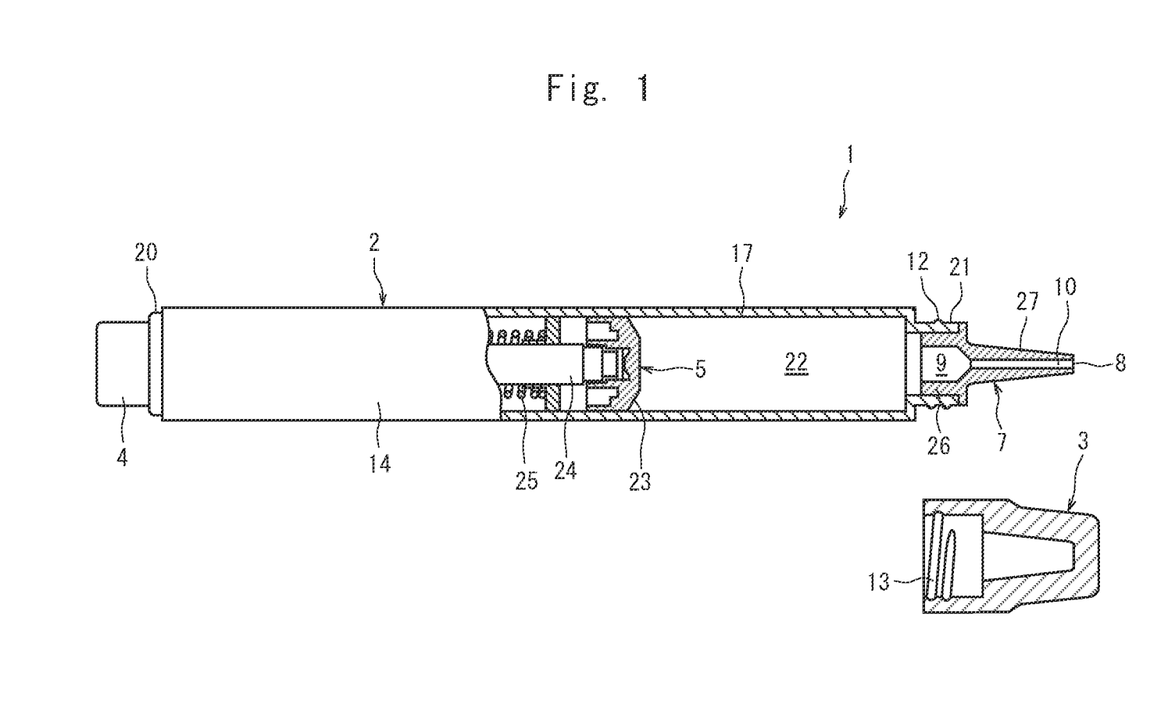
FIG. 1 is a partly cut-away front view of a knock-type ejection container according to an embodiment of the present invention.

FIG. 1 shows a knock-type ejection container 1 according to a first embodiment of the invention.

In FIG. 1, the upper part of the knock-type ejection container 1 is referred to as the front end (or front) and the lower part thereof is referred to as the rear end (or rear) (the same also holds in FIGS. 2, 4, 5 and 7).

The knock-type ejection container 1 works to eject a predetermined amount of a liquid which is contained in the knock-type ejection container 1 from an ejection port responsive to one time of pushing operation instead of propelling a core from the pen point by a predetermined amount of length responsive to one time of operation that is the case of a push-type knock button of a propelling pencil.

The knock-type ejection container 1 includes a container body 2, a cap 3, a knock button 4, and a knock mechanism 5. This embodiment describes the knock-type ejection container 1 that contains a dental bonding material. Though the content contained in the knock-type ejection container 1 is not limited to a dental bonding material, the knock-type ejection container 1 is capable of ejecting the solution in a predetermined amount, and is preferably used for containing an expensive liquid dental material such as the above-mentioned dental bonding material.

The container body 2 is forming a cylindrical circumferential wall 17 and a support portion 21 on which an ejection portion 7 is to be mounted on the front end side of the circumferential wall 17. The support portion 21 has a diameter smaller than that of the circumferential wall 17. The container body 2 is made of a synthetic plastic such as polyethylene, polypropylene, nylon or ethylene.vinyl alcohol copolymer. The container body 2 may be made of any material that does not affect the content such as a dental bonding material that is contained in the container body 2. When a material other than the dental bonding material is to be contained, the container body is similarly made of a material that will not affect the content.

The ejection portion 7 is provided on the front end side of the container body 2. The ejection portion 7 may be formed integrally with the container body 2 or may be attached thereto as a separate member. In this embodiment, the ejection portion 7 is attached as a separate member to the container body 2.

The ejection portion 7 includes a mounting portion 26 and a nozzle portion 27, the mounting portion 26 having an outer diameter which is equal to the inner diameter of the container body 2. The ejection portion 7 is mounted with the mounting portion 26 being inserted in an opening of the container body 2.

Here, the mounting portion 26 can be omitted when the container body 2 and the ejection portion 7 are integrally formed together.

In the nozzle portion 27, a flow passage 10 is penetrating through the central position of the nozzle portion 27 and maintains the same diameter up to an ejection port 8 at the nozzle end portion. The diameter of the ejection port 8 and the flow passage 10 is such that the material is not ejected despite the end of the nozzle portion 27 is faced down and that the material which is the content falls down in drops like the content in a container such as of eye lotion when an external force (in this embodiment, pushing force of a piston 23 that will be described later) is applied. The ejection port 8 is communicated with an ejection chamber 9 through the flow passage 10.

The ejection chamber 9 is formed in the mounting portion 26 of the ejection portion 7, the mounting portion 26 being mounted into a support portion 21 of the container body 2. An external thread 12 is formed on the outer circumferential surface of the support portion. The external thread 12 is screwed with an internal thread 13, which is formed on the inner surface of the cap 3 for closing the ejection port 8.

Referring to FIG. 1, a container chamber 22 for containing a liquid dental material is formed inside the circumferential wall 17 of the body portion 14 of the container body 2 on the ejection portion 7 side. The container chamber 22 has a circular shape in cross section, is communicated with the ejection chamber 9 on the ejection portion 7 side at the front end side, and is provided with a knock mechanism 5 on the knock button 4 side on the rear end side of the container body 2. The container chamber 22 so varies that the volume thereof decreases by an equal amount responsive to the knock mechanism 5. The knock mechanism 5 may be a conventional knock mechanism and is provided with the piston 23 facing the container chamber 22, the piston 23 having an outer circumferential portion that is in close contact with the inner circumferential surface of the container chamber 22. The piston 23 is provided with a rod 24 on the back surface thereof. Upon each push of the knock button 4, the piston moves forward by a predetermined amount, and the knock button 4 is returned back to the initial position due to a coil spring 25.

Next, described below is the operation of the embodiment.

Though there is no specific limitation on the liquid materials that are to be contained in the knock-type ejector container 1, desired materials are those having relatively low volatilities inclusive of dental materials. Concretely, preferred liquid materials are those liquid materials without containing volatile solvents (solvents having boiling points of not higher than 90° C.) that will be described later or those liquid materials containing volatile solvents but in amounts of less than 10% by mass, the liquid materials comprising chiefly a solvent having a boiling point of not lower than 90° C. and, more preferably, having a boiling point of not lower than 100° C., such as water, butanol, diethylketone, etc. The liquid materials having small volatilities are, specifically, the liquids having vapor pressures of lower than 30 hPa at 20° C.

To use the knock-type ejection container 1, the cap 3 is removed, and the body portion 14 is held by four fingers of either the right hand or the left hand, usually, with the inner surface of the thumb being put to the top surface of the knock button 4 since the container is of the knock type. Next, the front end of the ejection portion 7 is positioned just over a pick-up dish, a mixing paper or a desired portion such as diseased part. After the positioning has been completed, the knock button 4 is pushed by the thumb. In the knock-type ejection container 1, the piston 23 moves forward by an equal amount for each push, and the liquid which is contained is ejected in an equal amount each time.

When the dental material is to be fallen down in drops by one time of operation, the piston 23 moves forward by a predetermined distance. Here, when the knock button 4 that is pushed returns back, the piston 23 may have been so formed as to simultaneously (or not necessarily simultaneously) return back by a small amount from the position it has moved forward.

If the piston 23 remains moved forward after the dental material has been fallen down in drops by pushing the knock button 4, then the dental material after having been fallen down in drops remains and closes the flow passage 10. If the dental material remains in the flow passage 10 and is volatilized, in case that the air remains in the ejection chamber 9 or in the container chamber 22, then the interior of the container is hermetically closed and the pressure increases as the dental material volatilizes often causing the liquid remaining in the flow passage 10 to gush out from the ejection port 8. After the dental material has been fallen down in drops by pushing the knock button 4, if the liquid in the flow passage 10 is returned back into the ejection chamber 9 by moving the piston back to a degree that no liquid remains in the flow passage 10, then it is made possible to prevent the liquid from gushing out. Therefore, the amount of moving the piston 23 back may be so determined that the liquid remaining in the flow passage 10 returns back into the ejection chamber 9 by taking the volume of the flow passage 10 and the like into consideration.

As another mode, when the liquid is to be fallen down in drops from the container body 2 directly onto the diseased part or onto a separate saucer or the like, the ejection port 8 of the ejection portion 7 is pinpointed just on a desired portion, and the knock button 4 is pushed a plurality of times, e.g., two times to let the liquid fall in drops from the ejection port 8.

The container may be so designed that the liquid is ejected from the ejection port 8 due to the piston 23 that is moved forward upon one time of knock button operation but does not still fall down in drops from the ejection port 8 by the one time of forward movement of the piston; i.e., the container may be so designed that only one drop falls down from the ejection port 8 after the piston 23 is moved forward twice due to the operation of pushing the knock button 4 twice. Namely, a nucleus of drop is formed by pushing the knock button for the first time and, after the knock button is pushed for the second time, the nucleus is grown to a size large enough to drop. In the second to fourth embodiments that will be described below, too, though not described, the drops may be fallen down upon pushing the knock button a plurality of times (this will be described again in detail in the fifth embodiment.

Figure 2:
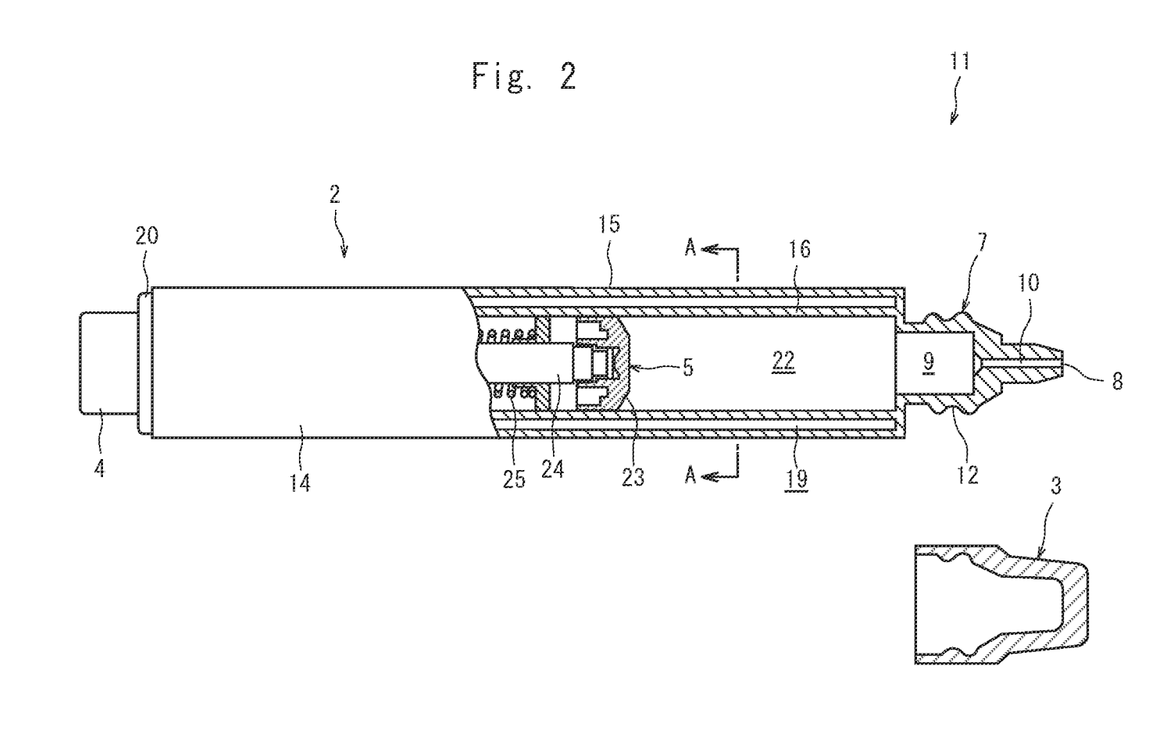
FIG. 2 is a partly cut-away front view of the knock-type ejection container according to a second embodiment of the present invention.

FIG. 2 shows a knock-type ejection container 11 according to a second embodiment of the invention.

The knock-type ejection container 11 includes the container body 2, cap 3, knock button 4 and knock mechanism 5. In this embodiment, the knock-type ejection container 11 is described as to contain a dental material.

The container body 2 can be made of a synthetic plastics such as polyethylene, polypropylene, nylon or ethylene.vinyl alcohol copolymer; i.e., the container body 2 can be made of any material that will not affect the content such as the dental material contained in the container body 2. This embodiment deals with the container that contains the dental material and specifically the material which is highly volatile.

The container body 2 is provided, on the front end side thereof, with the ejection portion 7 that becomes narrow toward the end, and the flow passage 10 of a small diameter is penetrating through the center of the ejection portion 7. The diameter of the ejection port 8 and the flow passage 10 is of such a size that the dental material falls down drop by drop like that of the container for eye lotions. The ejection port 8 is communicated with the ejection chamber 9 through the flow passage 10.

The ejection chamber 9 is provided on the proximal end side of the ejection portion 7, and an external thread 12 is formed on the outer side of the circumferential wall thereof. The cap 3 is screwed onto the external thread 12 to close the ejection port 8.

Figure 3:
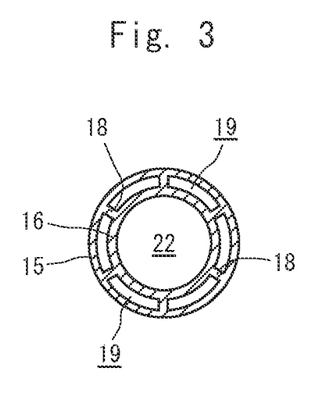
FIG. 3 shows ribs formed in the air chambers of the knock-type ejection container of FIG. 2, and is a sectional view along the line A-A in FIG. 2.

The body portion 14 of the container body 2 neighboring the ejection portion 7 has an outer diameter larger than that of the ejection portion 7. The body portion 14 includes an outer circumferential wall 15 and an inner circumferential wall 16. A gap is formed between the outer circumferential wall 15 and the inner circumferential wall 16 (denoted by the same reference numerals as those of the circumferential walls of FIG. 1. Referring to FIG. 3, a plurality of ribs 18 (see FIG. 3) are formed in the axial direction of the container body 2 to couple the outer circumferential wall 15 and the inner circumferential wall 16 together, and are extending from the front end portion of the body portion 14 of the container body 2 (from the side of the ejection portion 7) to the rear end portion thereof (to the side of the knock button 4). Between the outer circumferential wall 15 and the inner circumferential wall 16, there are formed a plurality of air chambers 19 being surrounded by the outer circumferential wall 15, inner circumferential wall 16 and ribs 18, 18 (FIG. 3). When the container body 2 is being formed, the air chambers 19 are formed open on their one side or on their both side in the axial direction of the container body 2 so that the metal mold can be removed. In this case, the open ends may be closed with some means such as a cap member 20. The air chambers 19, however, need not necessarily be closed spaces.

When the container body 2 is made of, for example, a relatively hard material, the air chambers 19 may be formed in the shape of one annular air chamber as a whole without ribs 18, and the ribs may be formed in the body portion 14 on the side of the knock button 4 only. Though a variety of structures can be contrived, what is necessary is that a sufficiently large heat-insulating space is present between the outer circumferential wall 15 and the inner circumferential wall 16. In this sense, the width of the ribs 18 is better small in the circumferential direction of the container body 2 from the standpoint of heat-insulating effect, and their number is better small, too. The widths of the ribs 18 should be determined to be small by taking the hardness of the material of the container body 2 and the like into consideration. In order to obtain a sufficient degree of heat-insulating effect, it is desired that the air chambers 19 are formed maintaining a width of 0.5 to 5 mm and, preferably, 1 to 3 mm in the radial direction of the container body 2.

The container chamber 22 is formed in the inner circumferential wall 16 of the body portion 14 of the container body 2 on the ejection portion 7 side to contain the liquid dental material. The container chamber 22 is circular in cross section, is communicated with the ejection chamber 9 on the ejection portion 7 side, and is provided with the knock mechanism 5 on the knock button 4 side. Due to the knock mechanism 5, the container chamber 22 varies in one direction such as reducing the volume thereof. The knock mechanism 5 may be a known one and is provided with the piston 23 that faces the container chamber 22, the piston 23 being arranged in the container chamber 22 with its outer circumferential portion in close contact with the inner circumferential surface of the container chamber 22. The piston 23 is provided on the back surface thereof with a rod 24 and is so constituted that upon pushing the knock button 4, the piston moves forward by only a predetermined amount for each push. The knock button 4 moves to the initial position due to a coil spring 25.

Next, the operation of the embodiment will be described.

It is desired that the liquid contained in the knock-type ejection container 11 is the one having volatility since it exhibits the effect of the invention of improving the flow down of liquid drop by drop. Here, the liquid having volatility is a liquid containing a volatile solvent that has a boiling point of not higher than 90° C., more preferably, not higher than 80° C. and, particularly desirably, 30 to 70° C. Further, the content of the volatile solvent is not less than 10% by mass and, preferably, not less than 40% by mass. The liquid having volatility can be effectively dropped when the vapor pressure thereof is not lower than 30 hPa at 20° C.

Concrete examples of the liquid inclusive of the dental material adapted to be contained in the container of the invention include alcohols such as methanol, ethanol and 2-propanol; ketones such as acetone and methyl ethyl ketone; ethers such as ethyl ether and tetrahydrofurane; esters such as ethyl acetate and ethyl formate; chlorinated solvents such as methylene chloride and the like; and fluorinated solvents such as trifluoroethanol and the like. These liquids are preserved at normal temperature or often in a refrigerator.

At the time of use, the knock-type ejection container 11 has been filled with a predetermined amount of volatile dental material. To use it, the cap 3 is removed, and the body portion 14 is held by four fingers of either the right hand or the left hand, usually, with the inner surface of the thumb being put to the top surface of the knock button 4 since the ejection container is of the knock type. Next, the front end of the ejection portion 7 is positioned just over a pick-up dish, a mixing paper or a desired portion such as diseased part. After the positioning has been completed, the knock button 4 is pushed by the thumb. In the knock-type ejection container 11, the piston 23 moves forward by an equal amount for each push, and the dental material can be fallen down in drops in a desired amount onto the desired portion.

In the conventional containers for dental materials, the body portion of the container was pushed being held by fingers, and the liquid was suitably fallen down in drops relying upon the pushing force based on the sense of fingertips and the depressed amount of the container. With the knock-type ejection container, the piston moves forward upon simply pushing the knock button offering an advantage of enabling the dental material to be fallen down in drops in a predetermined amount without relying upon the pushing force based on the sense of fingertips or the depressed amount of the container.

Due to the nature of the knock-type ejection container, however, the knock-type ejection container is in most cases held by putting the thumb on the knock button and gripping the body portion of the container body by the rest of four fingers. Therefore, the body temperature of the human fingertips and of the palm of the hand is conducted to the interior of the container containing the dental material through the whole circumference of the container walls. When a highly volatile liquid is handled, in particular, the pressure in the container rises due to the volatilization of liquid in the container and the dental material often falls down in drops in excess amounts from the ejection port of the knock-type ejection container.

In the knock-type ejection container 11 of this embodiment, air chambers 19 are formed in the body portion 14 of the container body 2. As is well known, the air has a large heat-insulating effect, shuts off the human body temperature conducted to the outer circumferential wall 15, and prevents or suppresses the heat from being conducted to the inner circumferential wall 16. Therefore, the temperature does not rise in the container chamber 22, the volatile liquid does not volatilize, the pressure does not increase in the container chamber 22, and the liquid is prevented from naturally flowing down in drops through the ejection port 8 of the container body 2. As a result, the dental material can be fallen down in drops in a predetermined amount onto the desired portion.

Specifically, in a state where the knock-type ejection container 11 is preserved in a refrigerator, a temperature differential of 20 to 30° C. may often occur. In such a case, the effect of heat insulation is exhibited by the air.

Even in case the knock-type ejection container 11 is not gripped by the hand of a dentist but is left in a lying manner with the cap member 20 being removed, the dental material is prevented from gushing out of the ejection port 8 of the ejection portion 7 and is not wasted.

Figure 4:
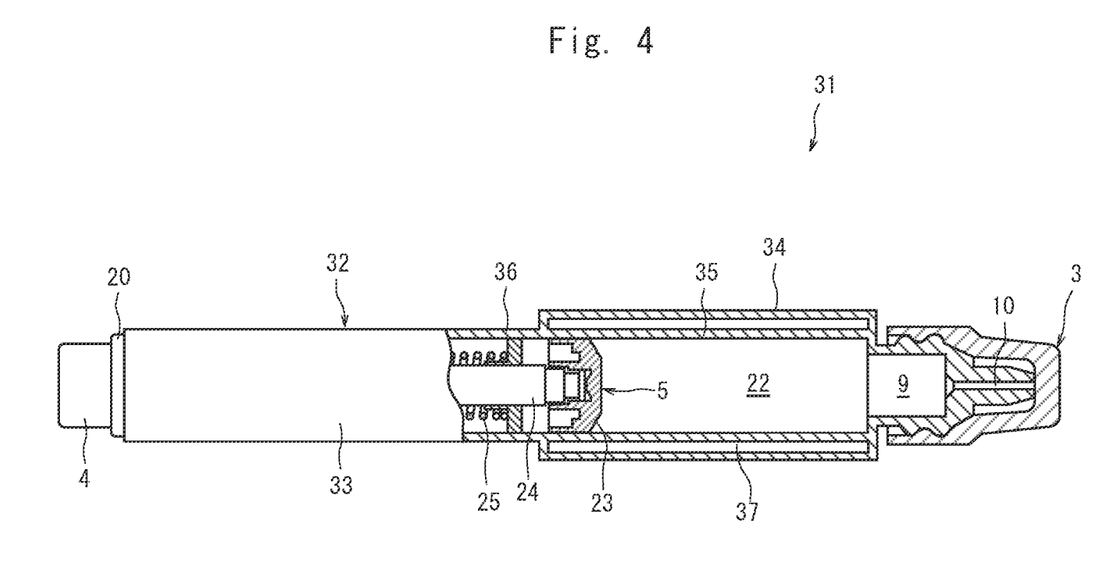
FIG. 4 is a partly cut-away front view of the knock-type ejection container according to a third embodiment of the present invention.

Next, described below is the knock-type ejection container according to a third embodiment of the present invention.

The same portions of the structure as those of the above second embodiment are denoted by the same reference numerals.

Referring to FIG. 4, a body portion 33 of a container body 32 of a knock-type ejection container 31 is forming an outer circumferential wall 34 and an inner circumferential wall 35 in nearly a half region of the body portion 33 on the side of the ejection portion 7. Therefore, a half region of the body portion 33 on the side of the knock button 4 has a circumferential wall 36 consisting of a single wall.

Air chambers 37 are formed between the outer circumferential wall 34 and the inner circumferential wall 35. In the body portion 33, the air chambers 37 must be formed from the front end of the container body 2 to the rear end side, i.e., to at least the side portion of the piston 23 in a state where the piston 23 is at the rearmost end position (initial position). Though not diagrammed, ribs similar to those of the above second embodiment are formed in the air chamber 19 in this embodiment (see ribs 18 in FIG. 3).

Other portions are the same as those of the second embodiment and are not described.

Being constituted as described above, the knock-type ejection container 31 of this embodiment is used in the same manner as that of the second embodiment. In this embodiment, the air chambers 37 are formed surrounding the container chamber 22 only. Despite the knock-type ejection container 31 is gripped, however, the container chamber 22 is surrounded by the air chambers 37 at all times preventing the temperature in the container chamber from rising due to the heat-insulating material which is the air. The other effects are the same as those of the second embodiment.

In this embodiment, too, the knock-type ejection container lets the liquid fall down in drops in suitable amounts from the container body without relying on the gap of human fingertips, and the container chamber has been so designed that the temperature therein will not vary.

Next, the knock-type ejection container according to a fourth embodiment of the invention will be described with reference to FIGS. 5 and 6.

Figure 5:
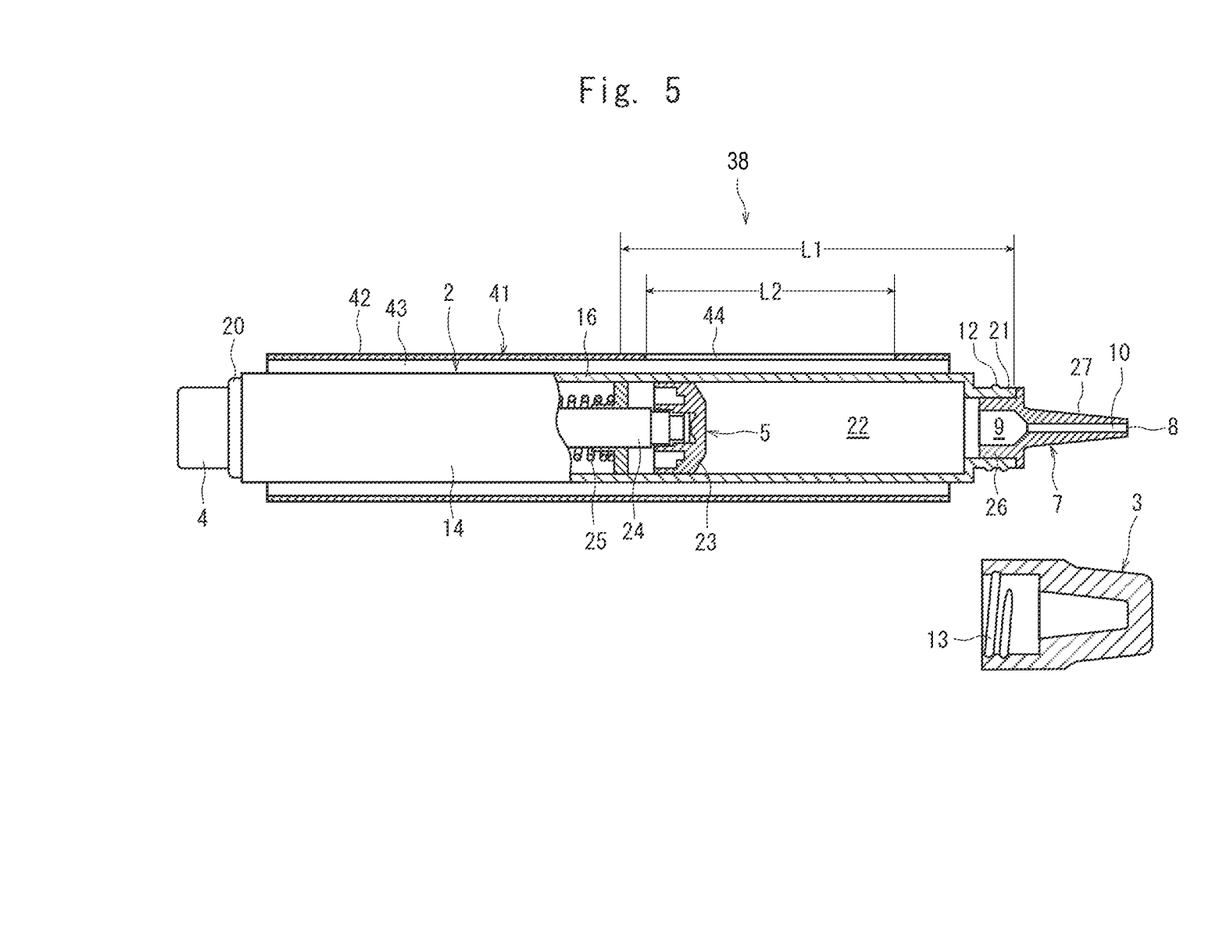
FIG. 5 is a partly cut-away front view of the knock-type ejection container (with a cylindrical heat-insulating material being fitted to the knock-type ejection container of FIG. 1) according to a fourth embodiment of the present invention.
Figure 6:
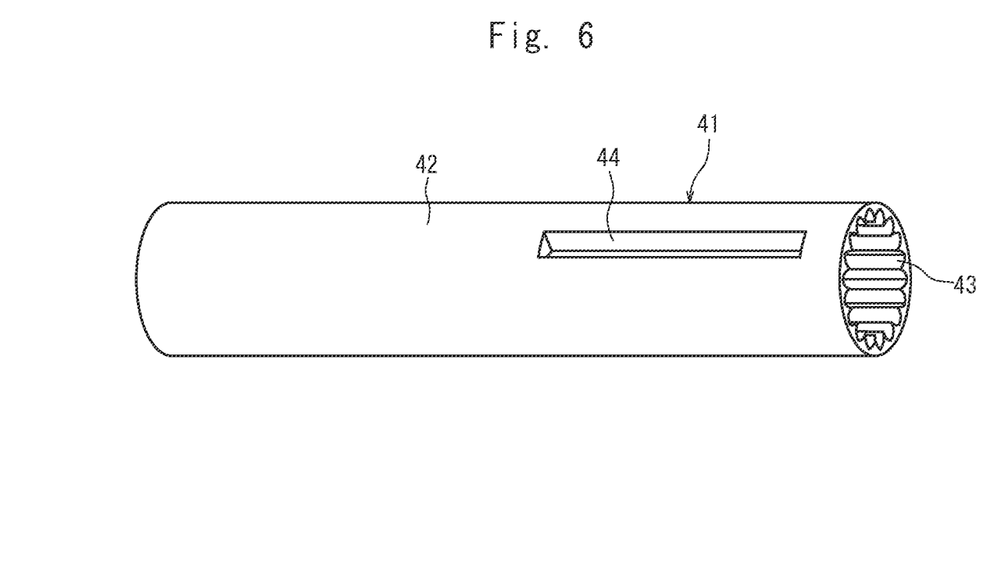
FIG. 6 is a perspective view of the heat-insulating material in FIG. 5.

The knock-type ejection container 38 of the embodiment shown in FIG. 5, is the knock-type ejection container 1 of the above first embodiment but to which a heat-insulating member 41 shown in FIG. 6 is detachably attached thereto.

Referring to FIG. 6, the heat-insulating member 41 is of a cylindrical shape forming a plurality of straight longitudinal ribs 43 on the inner circumferential surface of the circumferential Wall (outer circumferential Wall) 42 of the heat-insulating member 41 over one end to the other end of the outer circumferential Wall 42 in the axial direction. The length (inner diameter) across the ends of the longitudinal ribs 43 in the direction in which they are protruding (inside in the radial direction) is nearly equal to the outer diameter of the circumferential Wall 16 of the knock-type ejection container 38.

In this embodiment, the circumferential wall 16 of the container body 2 is formed of a transparent material over a range L1 shown in FIG. 5, and the heat-insulating member 41 has a slit 44 formed therein or is formed of a transparent member as shown in FIG. 6 over a range L2 so that the position of the piston 23 can be seen.

If the dental material to be contained in the container chamber 22 is not volatile, then the knock-type ejection container 38 of this embodiment shown in FIG. 5, does not have to use the heat insulating member 41 just like the knock-type ejection container 1 of the first embodiment. If the dental material to be contained in the container chamber 22 is volatile, however, the knock-type ejection container 38 of this embodiment shown in FIG. 5, uses the heat-insulating member 41.

The heat-insulating member 41 is forming longitudinal ribs 43 and gaps among the longitudinal ribs 43. With the heat-insulating member 41 being fitted to the container body 2, therefore, the air enters into between the circumferential wall 16 and the circumferential wall 42 to produce the heat-insulating effect. Besides, the position of the piston 23 can be seen through the slit 44 to confirm the amount of the dental material that is remaining.

In the first to third embodiments and in the embodiment of FIG. 5, too, the whole or part of the circumferential wall of the container body may be made transparent and a slit may be formed in the circumferential wall of the heat-insulating member, or the whole or part of the circumferential wall may be made transparent so that the amount of the dental material that is remaining can be seen.

Figure 7:
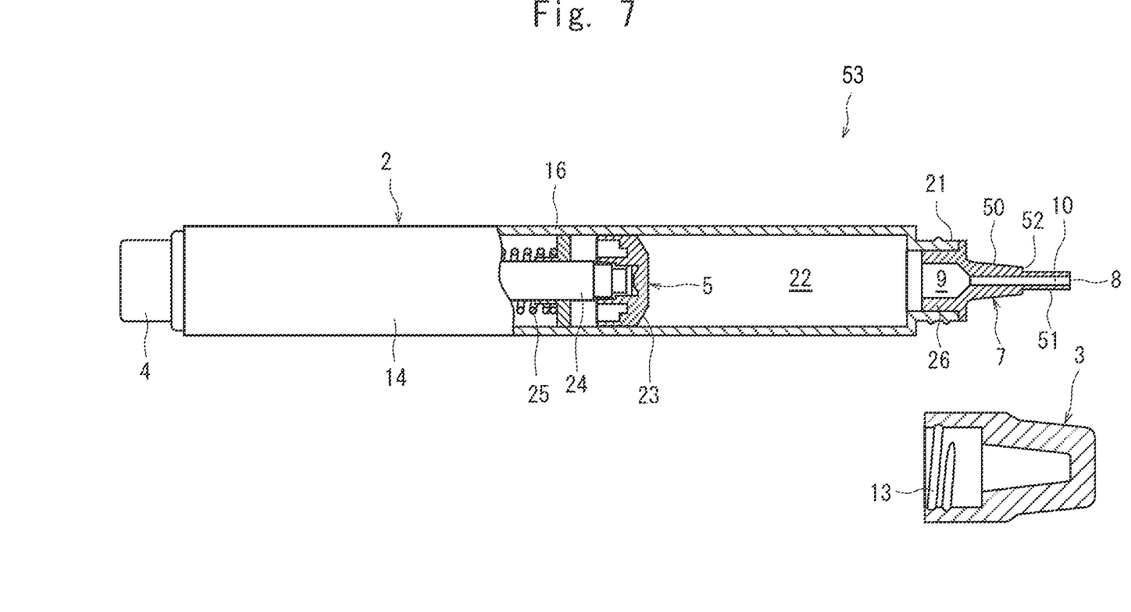
FIG. 7 is a partly cut-away front view of the knock-type ejection container according to a fifth embodiment of the present invention.

FIG. 7 shows the knock-type ejection container 53 according to a fifth embodiment of the invention, similar to the knock-type election container 1 of the first embodiment.

The knock-type ejection container 53 is the one that ejects, through its ejection port, a predetermined amount of liquid that is contained therein responsive to one time of pushing operation instead of propelling, through the pen point, a core by a predetermined length responsive to one time of operating the push-type knock button such as of a propel-ling pencil.

The knock-type ejection container 53 includes the container body 2, cap 3, knock button 4 and knock mechanism 5. The embodiment describes the knock-type ejection container 53 that contains a dental bonding material. Though the content contained in the knock-type ejection container 53 is not limited to a dental bonding material, the knock-type ejection container 53 is capable of ejecting the solution in a predetermined amount, and is preferably used for containing an expensive liquid dental material such as the above-mentioned dental bonding material.

The container body 2 is forming a cylindrical circumferential wall 16 and a support portion 21 in which the ejection portion 7 is to be mounted on the front end side of the circumferential wall 16. The support portion 21 has a diameter smaller than that of the circumferential wall 16. The container body 2 may be made of a synthetic plastics such as polyethylene, polypropylene, nylon or ethylene.vinyl alcohol copolymer. The container body 2 may be made of any material that does not affect the content such as the dental bonding material that is contained in the container body 2. When a material other than the dental bonding material is to be contained, the container body is made of a material that will not affect the content.

The ejection portion 7 is provided on the front end side of the container body 2. The ejection portion 7 may be formed integrally with the container body 2 or may be attached thereto as a separate member. In this embodiment, the ejection portion 7 is attached as a separate member to the container body 2.

Figure 8:
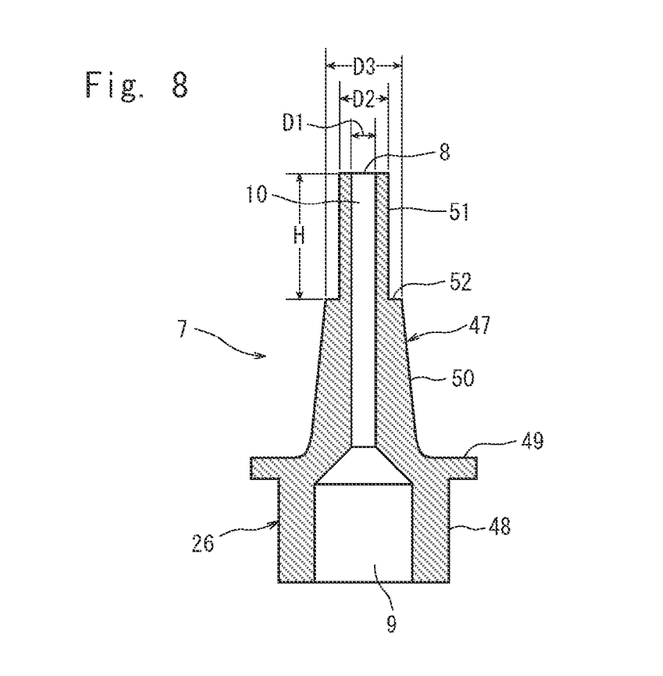
FIG. 8 is an enlarged sectional view of an ejection portion of the knock-type ejection container of FIG. 7.

FIG. 8 is an enlarged sectional view of the ejection portion 7. The ejection portion 7 includes the mounting portion 26 and the nozzle portion 47, the mounting portion 26 having an insertion portion 48 of a cylindrical shape in cross section and a flange 49. The insertion portion 48 has an outer diameter which is equal to the inner diameter of the container body 2 and is mounted by being inserted in the container body 2. The flange 49 is an annular flange that protrudes outward in the radial direction beyond the outer circumference of the insertion portion 48, and plays the role of a stopper after the insertion portion 48 has been inserted in the container body 2.

Here, the mounting portion 26 is omitted when the container body 2 and the ejection portion 7 are integrally formed together.

The nozzle portion 47 is provided on the front side of the flange 49 neighboring thereto, and includes a nozzle body 50 and a nozzle end portion 51. The nozzle body 50 has an outer surface that is tapered, the diameter thereof decreasing toward the front end side to arrive at the front end portion 51. In this embodiment, the nozzle end portion 51 is of a cylindrical shape having a diameter which is the same from the rear end thereof to the ejection portion 8 at the front end thereof. In the nozzle portion 47, the flow passage 10 is penetrating through the central position of the ejection portion 7 and is maintaining the same diameter from the nozzle body 50 up to the nozzle end portion 51. The diameter of the ejection port 8 and the flow passage 10 is such that the material is not ejected despite the end of the nozzle portion 27 is faced downward and that the material which is contained falls down in drops like the material contained in a container such as of eye lotion when an external force is applied (in this embodiment, pushing force of the piston 23 that will be described later). The ejection port 8 is communicated with the ejection chamber 9 through the flow passage 10.

Figure 9:
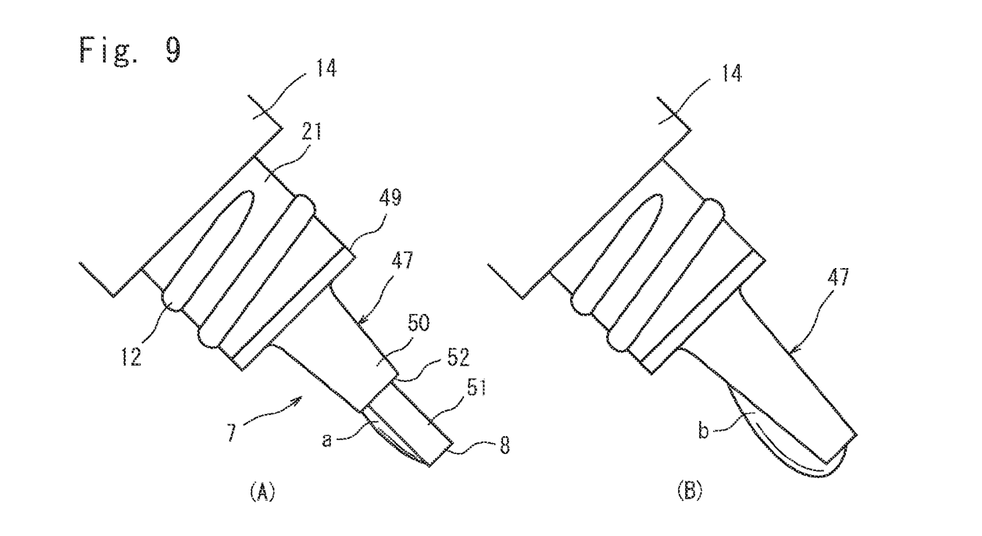

The ejection chamber 9 is formed in the mounting portion 26 of the ejection portion 7, the mounting portion 26 being mounted in the support portion 21 of the container body 2. The external thread 12 is formed on the outer circumferential surface of the support portion. Onto the external thread 12 shown in FIG. 9 is screwed the internal thread 13 (FIG. 7) formed in the inner surface of the cap 3 that closes the ejection port 8, and the ejection port 8 is closed by the cap 3.

The stepped surface 52 is formed at a boundary portion between the nozzle body 50 and the nozzle end portion 51. Namely, the stepped surface 52 is a flat annular surface formed from the rear end of the nozzle end portion 51 toward the outer side of the nozzle end portion 51 in the radial direction, and is continuous to the edge of the tapered surface of the nozzle body 50. Therefore, the stepped surface 52 is facing the front end side of the nozzle portion 47.

The stepped surface 52 is provided to prevent the drops, that are ejected from the ejection port 8 of the nozzle portion 47 but remain adhered to the periphery of the ejection port 8 without falling down, from creeping toward the rear end side of the nozzle body 50 and to prevent the drops that are adhering from mixing together and excessively growing.

Therefore, the length from the nozzle end portion 51 to the stepped surface 52 is required to be formed smaller than a maximum length which the liquid that did not fall down may creep. As for the width of the annular stepped surface 52 in the radial direction, if the width of the annular stepped surface 52 in the radial direction is too broad, the liquid flows down along the stepped surface 52 when the container body 2 is used with its front end side being tilted downward and, therefore, the liquid drips down from the corner portion between the stepped surface 52 and the nozzle body 50 or the liquid stays being slackened toward the nozzle body 50. Therefore, the width of the stepped surface 52 should be so determined as will not be affected thereby. If the step is too small, however, the liquid creeps. Therefore, the width of the annular stepped surface 52 in the radial direction should be suitably determined by taking the above phenomena into consideration.

Next, the sizes of the nozzle portion 47 and the stepped surface 52 will be concretely described.

If the amount (volume) of a drop discharged from the ejection portion 7 and falling down due to the knock button push operation is denoted by V, the inner diameter of the ejection port of the nozzle end portion 51 in the ejection portion 7 shown in FIG. 8 by D1, the outer diameter of the ejection port of the nozzle end portion 51 by D2, the outer diameter of the stepped surface 52 by D3, and the length from the ejection port 8 of the nozzle end portion 51 to the stepped surface 52 by H, then D1, D2, D3 and H can be set as follows:

The inner diameter D1 of the ejection port of the nozzle end portion 51 is $aV^{1/3}$ (a is in a range from 0.5 to 0.7), i.e., in a range of $0.5V^{1/3} \leq D1 \leq 0.7V^{1/3}$;

The outer diameter D2 of the ejection port of the nozzle end portion 51 is $bV^{1/3}$ (b is in a range from 0.8 to 1.1), i.e., in a range of $0.8V^{1/3} \leq D2 \leq 1.1V^{1/3}$;

The outer diameter D3 of the stepped surface 52 is $cV^{1/3}$ (c is in a range from 1.3 to 1.7), i.e., in a range of $1.3V^{1/3} \leq D3 \leq 1.7V^{1/3}$; and The length H from the ejection port 8 of the nozzle end portion 51 to the stepped surface 52 is $dV^{1/3}$ (d is in a range from 1.0 to 1.2), i.e., in a range of $1.0V^{1/3} \leq H \leq 1.2V^{1/3}$.

The inner diameter D1 and the outer diameter D2 of the ejection port of the nozzle end portion 51 are set for the ranges of a and b in association with the ejection port 8 of the nozzle portion 47 that is normally used of the knock-type ejection container 1 and the volume V of a drop of the liquid that falls down. In the knock-type ejection container of the present invention, a preferred volume V of the drop of liquid that falls down is, usually, from 5 to 20 $mm^3$ when the content contained therein is a dental bonding material. In this case, therefore, D1 is preferably 0.9 to 1.9 mm and D2 is preferably 1.4 to 3.0 mm.

The outer diameter D3 of the stepped surface is determined in relation to the outer diameter D2 of the ejection port of the nozzle end portion 51 and to the volume V of a drop of liquid that falls down, and is of such a length that the liquid will not creep over the stepped surface 52. If the stepped surface 52 is too wide, the liquid tends to creep toward a corner portion between the stepped surface 52 and the nozzle body 50. Therefore, the width is set so as not to be affected by such creeping and the range of c set in association with the width and the volume V of a drop of the liquid that falls down. Therefore, the diameter D3 is preferably 2.2 to 4.6 mm when the content that is contained is a dental bonding material.

The length H from the ejection port 8 of the nozzle end portion 51 to the stepped surface 52 is set for the range of d in association with the length that the liquid creeps when the nozzle portion 47 is tilted downward and the volume V of a drop of liquid that falls down. The length H is preferably 1.7 to 3.3 mm when the content that is contained is a dental bonding material.

It is desired that D1, D2, D3 and H are all satisfying their ranges.

Referring to FIG. 7, the container chamber 22 for containing the liquid dental material is formed inside the inner circumferential wall 16 of the body portion 14 of the container body 2 on the ejection portion 7 side. The container chamber 22 is of a circular shape in cross section, is communicated with the ejection chamber 9 on the ejection portion 7 side, and is provided with the knock mechanism 5 on the side of the knock button 4. The container chamber 22 so varies that the volume thereof decreases by an equal amount due to the knock mechanism 5. The knock mechanism 5 may be a conventional knock mechanism and is provided with the piston 23 facing the container chamber 22, the piston 23 having an outer circumferential portion that is in close contact with the inner circumferential surface of the container chamber 22. The piston 23 is provided with the rod 24 on the back surface thereof. Upon each push of the knock button 4, the piston moves forward by a predetermined amount, and the knock button 4 is returned back to the initial position due to the coil spring.

According to this embodiment, the feature of the knock mechanism of the knock-type ejection container 53 resides in that the liquid is ejected from the ejection port 8 due to the piston 23 that has moved forward upon one time of knock button operation but does not still fall down in drops from the ejection port 8 by one time of forward movement of the piston. The liquid falls down in drops after the knock button 4 is operated a plurality of times (or after the piston 23 has moved forward a plurality of times). In this embodiment, one drop falls down from the ejection port 8 after the piston 23 has moved forward twice responsive to operating the knock button 4 twice.

Next, the operation of the embodiment will be described.

The liquids to be contained in the knock-type ejection container 1, i.e., concrete examples of the liquid suited for being contained in the container of the present invention, inclusive of dental materials, are alcohols such as methanol and ethanol; ketones such as acetone and methyl ethyl ketone; ethers such as ethyl ether and tetrahydrofurane; esters such as ethyl acetate and ethyl formate; chlorinated solvents such as methylene chloride, etc.; and fluorinated solvents such as trifluoroethanol, etc.

To use the knock-type ejection container 53, the cap 3 is removed, and the body portion 14 is held by four fingers of either the right hand or the left hand, usually, with the inner surface of the thumb being put to the top surface of the knock button 4 since the container is of the knock type. Next, the front end of the ejection portion 7 is positioned just over a pick-up dish, a mixing paper or a desired portion such as diseased part. After the positioning has been completed, the knock button 4 is pushed by the thumb. In the knock-type ejection container 53, the piston 23 moves forward by an equal amount for each push, and the liquid Which is contained is ejected in an equal amount each time.

When it is attempted to fall the liquid in drops down from the container body 2 directly onto a diseased part, the ejection port 8 of the ejection portion 7 is aimed at just on a desired portion, and the knock button 4 is pushed twice. Then the liquid falls in drops from the ejection port 8. When the container body 2 is vertically directed, the liquid creeps a little toward the nozzle end portion 51. When it is attempted to fall the liquid in drops down directly onto the tooth of a patient, however, the container body 2 is, inmost cases, used with the front end side thereof being tilted downward. Therefore, the liquid creeps when the container body is tilted and stays. Specifically, when the cap must be opened and closed for each use like the case of using the dental bonding material, undesired stay of the liquid makes it difficult to supply the liquid in a suitable amount or hinders the opening or closing of the cap in case the remaining liquid is left to stay. Therefore, the liquid had to be wiped off. Quite a few of the materials are expensive, depending on the material though, and the liquid that undesirably stays causes a loss in economy.

The liquid creeps differently depending on the viscosity of the liquid, wettability of the material of the container and tilt of the container body 2 and so on. When container body 2 is continuously operated, however, the liquid often creeps over a length of about two times of the diameter of the drop that falls down.

In this embodiment, the stepped surface is formed at a portion in such that the length from the end of the nozzle end portion 51 to the stepped surface 52 can be shorter than the length which the liquid may creep. Therefore, the liquid is interrupted by the stepped surface 52 and does not creep beyond the stepped surface 52. Usually, the liquid that stays is wiped out each time. In case the container body is continuously used without wiping, however, the stay of liquid increases. When no stepped surface has been formed, the stay of liquid grows up to a size of about twice as large as the drop of liquid that falls down if the container body 2 is maintained tilted downward. In this embodiment in which the stepped surface 52 has been formed, the creeping of liquid is limited. Namely, as shown in FIG. 9A, the stay of liquid (a) is allowed to grow in a narrow area, i.e., grows only a little.

With the knock-type ejection container 53, the liquid can be fallen down in drops responsive to one time of knock button operation and the liquid does not creep due to the stepped surface 52. However, a drop of liquid must be necessarily fallen down by operating the knock button only once. For this purpose, a drop must be ejected in an increased amount. That is, in order for a drop of liquid to be necessarily fallen down through one time of operation, the amount of ejection is set to be larger than the amount (minimum amount) necessary for letting the liquid to drop. Often, however, the liquid that is ejected may not all fall down but may creep around the nozzle end portion 51 and stays thereon.

In this embodiment, a drop of liquid falls down upon pushing the knock button 4 twice. Namely, a nucleus of drop is formed upon the first push of the knock button, and the nucleus is grown upon second push of the knock button to a size large enough to fall down. Thus the knock button is operated twice (a plurality of times) so that the drop does not grow suddenly but grows and falls down after operated a plurality of times.

Even if what is regarded as a nucleus creeps around the nozzle end portion 51 and stays as liquid stay a, the liquid that is staying does not creep any more due to the stepped surface 52 but remains at a relatively lower part of the nozzle portion 47. Due to the operation of the second time, the liquid stay a that is staying mixes with the liquid that is ejected and falls down together.

With the conventional container for containing dental material as taught in the patent document 1 described earlier, the body portion of the container is pushed by being held by fingers and is adjusted relying on the sense of pushing by fingertips. With the knock-type ejection container of the present invention, on the other hand, the piston moves forward upon simply pushing the knock button offering an advantage in that the dental bonding material of a predetermined amount can be fallen down in drops without relying on the sense of fingertips.

Besides, the end of the knock-type ejection container is of the nozzle type without using the brush ear that is used in the prior art, eliminating the need of renewing the brush ear for each patient from the hygienic point of view.

Though the embodiments of the invention were described above in detail with reference to the accompanying drawings, it should be noted that the invention is not limited to the above embodiments only and can be varied or modified in various other ways without departing from the scope of the invention.

In the above embodiments, for example, the air was used as the heat-insulating material between the outer circumferential wall 15, 34 and the inner circumferential wall 16, 35 of the container body 2, 32 of the knock-type ejection container and, for this purpose, the air chambers 19 were formed. As the heat-insulating portions, however, there may be used a solid heat-insulating material in addition to the gas such as the air. When a volatile dental material is to be contained, further, the circumferential wall 17 may be formed of a heat-insulating material even if the knock-type ejection container is the one of the above first embodiment.

When a highly volatile material is used in, for example, the fifth embodiment, the container body may be realized forming inner and outer double walls, forming a liquid container chamber on the inside and containing a heat-insulating material such as the air as a heat-insulating chamber on the outer side.

DESCRIPTION OF REFERENCE NUMERALS

1, 11, 31, 38, 53 knock-type ejection containers
2, 32 container bodies
3 cap
4 knock button
5 knock mechanism
7 ejection portion
8 ejection port
14 body portion
15, 34 outer circumferential walls
16, 33 circumferential walls (inner circumferential walls)
17, 42 circumferential walls
18, 43 ribs
19, 37 air chambers
22 container chamber
23 piston
41 heat-insulating material
44 slit
47 nozzle portion
50 nozzle body
51 nozzle end portion
52 stepped surface

The invention claimed is:

1. A knock ejection container with a knock mechanism in which an ejection nozzle is provided at a front end of a container body, a knock button is provided at a rear end of the container body, a container chamber is provided in the container body to contain a liquid dental bonding material, the container chamber provided with the knock mechanism being interlocked to a pushing operation of the knock button, and the liquid dental bonding material contained in the container chamber falls down in drops from the ejection nozzle due to the knock mechanism in response to the pushing operation of the knock button, and wherein the ejection nozzle includes a nozzle end portion on the front end, an ejection port at the front end thereof, a nozzle body on the rear end, and a stepped surface is formed at a boundary portion between the nozzle end portion and the nozzle body over the whole circumference of the nozzle end portion, the stepped surface having a diameter expanding from an outer circumferential surface of the nozzle end portion toward the outer side of the nozzle end portion in the radial direction, wherein an inner diameter D1 of the ejection portion is 0.9 mm to 1.9 mm, an outer diameter D2 of the ejection portion is 1.4 mm to 3.0 mm, a diameter D3 of the stepped surface is 2.2 mm to 4.6 mm, and a length H from the ejection portion of the nozzle end portion to the stepped surface is 1.7 mm to 3.3 mm, wherein if the amount of a drop discharged from the nozzle portion by pushing operation of the knock button is denoted by V, the inner diameter of the ejection port of the nozzle end portion D1, the outer diameter of the ejection port of the nozzle end portion by D2, the outer diameter of the stepped surface by D3, and the length from the ejection port of the nozzle end portion to the stepped surface by H, then the inner diameter D1 of the ejection port is set to be $aV^{1/3}$ in which a is in a range from 0.5 to 0.7, the outer diameter D2 of the ejection port is set to be $bV^{1/3}$ in which b is in a range from 0.8 to 1.1, the outer diameter D3 of the stepped surface is set to be $cV^{1/3}$ in which c is in a range from 1.3 to 1.7, and the length H from the ejection port of the nozzle end portion to the stepped surface is set to be $dV^{1/3}$ in which d is in a range from 1.0 to 1.2, in a manner that D1, D2, D3 and H are all satisfied.

2. The knock ejection container according to claim 1, wherein the container body has the container chamber and a double-wall structure, the container chamber surrounded by the double-wall structure, and the double-wall structure comprising an inner circumferential wall and an outer circumferential wall, and a heat-insulating portion is provided between the inner circumferential wall and the outer circumferential wall.

3. The knock ejection container according to claim 2, wherein the heat-insulating portion is the air filled in gap portions formed between the outer circumferential wall and the inner circumferential wall.

4. The knock ejection container according to claim 2, wherein the outer circumferential wall is detachably fitted to the inner circumferential wall.

5. The knock ejection container according to claim 2, wherein at least part of the inner circumferential wall is formed of a transparent material enabling the amount of the dental bonding material contained therein to be recognized from the outer side of the outer circumferential wall, at least part of the outer circumferential wall is formed of a transparent material enabling the transparent portion of the inner circumferential wall to be recognized from the outer side of the outer circumferential wall, or a slit is perforated therein.

6. The knock ejection container according to claim 1, wherein a drop of liquid is fallen down from the ejection nozzle by the operation of pushing the knock button two or more times.

7. The knock ejection container according to claim 1, wherein the liquid dental bonding material is a dental bonding material.

8. The knock ejection container according to claim 1, wherein the knock mechanism is provided with a piston facing the container chamber and the piston moves forward by a predetermined amount upon each push of the knock button.

\* \* \* \* \*